United States Patent
Genkin et al.

(10) Patent No.: US 7,612,032 B2
(45) Date of Patent: *Nov. 3, 2009

(54) METHOD FOR TREATING ONCOLOGICAL DISEASES

(76) Inventors: Dmitry Dmitrievich Genkin, d.26, kv. 1, Saint-Petersburg, Konstantinovsky pr. (RU) 197110; Viktor Veniaminovich Tets, Saint-Petersburg, ul.Lensoveta, d.27, kv.95, Saint-Petersburg (RU) 196066; Gregory Viktorovich Tets, ul.Pushkinskaya, d.13, kv.41, Saint-Petersburg (RU) 191025

( * ) Notice: Subject to any disclaimer, the term of this patent is extended or adjusted under 35 U.S.C. 154(b) by 370 days.

This patent is subject to a terminal disclaimer.

(21) Appl. No.: 10/564,861

(22) PCT Filed: Jul. 1, 2004

(86) PCT No.: PCT/RU2004/000261

§ 371 (c)(1), (2), (4) Date: Jan. 12, 2006

(87) PCT Pub. No.: WO2005/004903

PCT Pub. Date: Jan. 20, 2005

(65) Prior Publication Data

US 2006/0233780 A1    Oct. 19, 2006

(30) Foreign Application Priority Data

Jul. 14, 2003   (RU) ................. PCT/RU03/00304
Mar. 12, 2004   (RU) ........................ 2004108061

(51) Int. Cl.
  *A61K 38/43*   (2006.01)
  *C12N 9/16*    (2006.01)
(52) U.S. Cl. ........................... 514/2; 435/196
(58) Field of Classification Search ............ None
  See application file for complete search history.

(56) References Cited

FOREIGN PATENT DOCUMENTS

WO    WO 01/074905    * 10/2001

OTHER PUBLICATIONS

Ngan et al. "Remarkable Application of Serum EBV EBER-1 in Monitoring Response of Nasopharyngeal Cancer Patients to Salvage Chemotherapy" Ann. NY Acad. Sci., 2001, 945, 73-79.*
Sugihara et al. "Deoxyribonuclease treatment prevents blood-borne liver metastasis of cutaneously transplanted tumour cells in mice," Br. J. Cancer, 1993, 67, 66-70.*
Ulrich & Friend "Toxicogenomics and drug discovery: will new technologies help us produce better drugs?" Nature, 2002, 1, 84-88.*
Ashton "Growing pains for biopharmaceuticals," Nature Biotech, 2001, 19, 307-311.*
Gibbs et al. "Mechanism-Based Target Identification and Drug Discovery in Cancer Research" Science, 2000, 287, 1969-1973.*
Shak et al. "Recombinant human DNAse I reduces the viscosity of cystic fibrosis sputum," Proc. Natl. Acad. Sci., 1990, 87, 9188-9192.*
Leland et al. "Cancer chemotherapy—ribonucleases to the rescue" Chem. & Bio., 2001, 8, 405-13.*
Nestle & Roberts "An extracellular nuclease from Serratia marcescens," J. Biol. Chem., 1969, 244, 5213-5218.*

* cited by examiner

*Primary Examiner*—Cecilia Tsang
*Assistant Examiner*—Christina Bradley
(74) *Attorney, Agent, or Firm*—John D. Gugliotta, PE, Esq

(57) ABSTRACT

A method to treat solid tumors and other oncological diseases consists of parenterally injecting an agent which destroy's blood's extracellular DNA into the systemic blood circulation of a cancer patient to slow down malignant. The agent is embodied in the form of a DNAse enzyme and, more particularly, as a bovine pancreatic DNAse. Doses from 50,000-250,000,000 Kunz units/day are injected for 5-360 days. A binding agent or an agent that modifies the chemical composition of the blood extracellular DNA is additionally injected into the blood. This modifying agent is preferably an enzyme-ribonuclease.

7 Claims, No Drawings

METHOD FOR TREATING ONCOLOGICAL DISEASES

RELATED APPLICATIONS

The present invention is a National Phase Filing of PCT/RU2004/00261. Additionally, the following copending applications are related to the present subject matter:

1. U.S. Ser. No. 10/564,609 for "Method for treating oncological, virulent and somatic diseases, method for controlling treatment efficiency, pharmaceutical agents and compositions for carrying out said treatment", filed on Jan. 12, 2006, which was a National Phase Filing of PCT/RU2003/000304;

2. U.S. Ser. No. 10/564,609 for "Method for Treating Diseases Associated with Changes of Qualitative and Quantitative Composition of Blood Extracellular DNA", filed on Jan. 12, 2006, which was a National Phase Filing of PCT/RU2004/00260; and 3. U.S. Ser. No. 11/919,141 for "Method for retarding unhealthy manifestations brought by ageing of human beings", filed on Oct. 23, 2007, which was a National Phase Filing of PCT/RU2005/000236.

The contents of the '615, '609 and '141 applications are incorporated by reference herein as if rewritten in their entirety.

FIELD OF THE INVENTION

The present invention generally relates to a method for treating oncological diseases by administering an agent that destroys extracellular DNA in the blood of a cancer patient.

BACKGROUND OF THE INVENTION

Populations of tumor cells developing in patients have a very high genetic variability which exceeds a same for healthy cells. Genetic variability of cancer cell populations causes mutated cells to generate phenotypes that (1) are insensitive to immune and morphogenetic control, (2) have an ability to invade and metastasize, and (3) are desensitized to cancer therapies. Selection and clonal expansion of cancer cells are both considered to underlie a biological and a clinical progression of tumors. For this reason, an approach of modem cancer therapies is based on a destruction of cancer cell clones in patients by means of chemotherapy, immunotherapy, biotherapy, surgical methods, or a combination thereof.

Chemotherapy, radiotherapy, biotherapy and more recent immunotherapy are the most commonly used non-surgical methods of treating cancer diseases. These therapies are administered to destruct, to damage or to inactivate a cancer cell's intracellular DNA.

The chemotherapy approach is based an administration of well known compounds: platinum preparations, antracycline antibiotics, alkylating agents and podophyllotoxins. The radioimmunotherapy approach is based on irradiation of intracellular DNA of cancer cells' nuclei. Alpha particles from alpha emitters are specially delivered into the cancerous cells to increase effects on those cells' intracellular DNA. Biotherapeutic and immunotherapeutic approaches are based on an induction of apoptosis of cancer cells, which induces death of the cancer cell. Apoptosis starts with an activation of intracellular nucleuses and follows with a degradation of the tumor cell's intracellular DNA. This process is accomplished, for example, by means of administering geno-therapeutic constructions that consist of genes that induce apoptosis or genes coding the factors which activate the nucleuses.

Aguilera, et al. discloses in U.S. Pat. No. 6,455,250 endonuclease Endo SR to treat cancer diseases by mode of its intracellular delivery into target cells. This method and chemotherapy, with Etopozide-4-Demetilpipodophylotoxe (4,6—O—R)-etiliden-b-D-glycopiranozid, were both selected for a prototype of the present invention.

Topoizomeraze II is an essential cell enzyme that regulates many aspects of DNA function. The enzyme is responsible for interconversion of different topological forms of intracellular DNA by means of a generation of transitory breaks of double-stranded DNA. Etopozide, as a Topoizomeraze II inhibitor, increases an intracellular level of "broken DNA-Topoizomeraze II" complexes.

The result of this drug's influence is an accumulation of double-stranded intracellular DNA breaks which lead to the cell's death. A drawback of this method prototype, along with well-known methods, is their low efficacy. These methods imply that mostly the cancer cells' intracellular DNA is the therapeutic target. Because of high genetic variability, these cancer cells become desensitized to the therapies before they are adequately eliminated. A further disadvantage is that the intracellular DNA is a difficult-to-approach target; it leads to necessary high-dosing antineoplastic chemotherapy and/or other complicated delivery systems. A final disadvantage to these methods is that they are highly toxic: their influence on cancerous cells' intracellular DNA also damages healthy cells' DNA.

SUMMARY OF THE INVENTION

An object of this invention is to develop a highly efficient cancer therapy having low toxicity. It is an object to resolve the foregoing drawbacks by administering into systemic circulation an agent which destroys blood extracellular DNA.

The agent is introduced in doses that alter an electrophoretic profile of blood extracellular DNA, which could be detectable by pulse-electrophoresis. Doses of the agent are introduced according to a regime schedule that provides for plasma hydrolytic activity exceeding 150 Kuntz units/liter of blood plasma. This level can be supported for more than 12 hours within a 24 hour period. The treatment is carried out continuously for no less than 48 hours. In particular, bovine pancreatic DNase can be introduced parenterally in doses ranging from 50,000 Kunitz per day to 250,000,000 per day. These doses are administered anywhere between five and 360 days. In particular, recombinant human Dnase (domase—alpha) can be parenterally introduced in doses ranging from 0.15 mg/day to 500 mg/day between a five-360 day period. The treatment may continue for a life of the patient. Additionally, an agent which bounds extracellular DNA, s.a., anti-DNA antibodies, can also be introduced to the systemic circulation. A modifying agent can further be introduced into the circulation, which modifies the chemical structure, the conformation, the degree of polymerization, or the association of proteins, lipids and/or ribonucleic acids of the blood's extracellular DNA. A preferred modifying agent may be a ribonuclease enzyme and, more particularly, Serratia Mercenses.

The present invention suggests that cancer can be treated by reducing circulating DNA levels. Circulating DNA levels are higher in the blood of cancer patients than in healthy controls. Stroun discloses in U.S. Pat. No. 5,952,170 a method of diagnosing cancers, wherein extracellular DNA in the blood is used for diagnostics and for a prognosis of a clinical course of a malignant disease. Hoon and Gocke disclose in U.S. Pat. Nos. 6,465,177 and 6,156,504, respectively, a use of blood's extracellular DNA to define mutations in oncogenes and microsatellic fragments of genes. These patents also disclose usages of blood's extracellular DNA for studying genome instability in tumors.

There is no systematic analysis of blood's extracellular DNA spectrum and its biological role prior to this invention. A search of the prior art reveals no published data concerning a research of blood's extracellular DNA performed without a polymerase chain reaction ("PCR"). Polymerase chain reactions can pervert a pattern of blood's extracellular DNA because of a specificity of primers which are used for amplification. Until recently, a genetic analysis of extracellular blood DNA was mainly carried out by PCR or by blot-hybridization and it was directed to a study of changes in certain fragments of a genome, s.a., e.g., microsatellites and separate genes during a malignant process.

There is thus no available knowledge about a genetic repertoire of blood's extracellular DNA in cancer patients, about a biological role of that blood's extracellular DNA in oncopatology, and about the potential therapeutic effects of a destruction, an inactivation or a treatment of these diseases.

The blood's extracellular DNA in cancer patients contains a unique quantitative and qualitative repertoire of genes and regulating genetic elements which greatly differ from that of DNA in a healthy human genome. In contract to intracellular DNA, extracellular DNA in cancer patients mainly contains unique human genes, including genes which are involved in a development of and a maintenance of malignant behavior in cancer cells. Because blood's extracellular DNA contributes to malignant growth in cancer patients, a destruction of, a modification of, or a binding of blood's extracellular DNA is useful because it slows down that growth. These interventions are very useful in independent therapy and they also increase an effectiveness of traditional methods of treatment.

The aforesaid new characteristics of this invention are based on new ideas about mechanisms of oncological diseases.

BRIEF DESCRIPTION OF THE DRAWINGS

As set for below the invention has been explained by detailed description of embodiments without references to drawings.

Preferred Embodiment

The inventive method is realized as followed:
Materials and Methods.

The following agents were used which destroys extracellular blood DNA: bovine pancreatic DNAase (Sigma and Samson Med), recombinative human DNAase 1 (Dornase alpha; Genetech), Serratia Mercenses extracellular nuclease. The solutions of DNA-se for administration was made by dissolving of mother solutions of DNA-se in sterile phosphate buffer just before administration.

Extracellular DNA from blood plasma was isolated as follows: fresh plasma (no more than 3-4 hours after sampling) was centrifuged on Ficoll-PlaquePlus (Amersham-Pharmacia) during 20 minutes at 1500 g at room temperature. ½ of plasma was detached, not affecting the rest of cells on the Ficoll pillow, and further centrifuged at 10000 g during 30 min for separation from cell fragments and debris. Supernatant was detached, without affecting of the sediment, and was toped up to 1% of sarkosil, 50 mM tris-HCl, pH 7,6, 20 mM EDTA, 400 mM NaCl, and than mixed with equal volume of phenol-chloroform(1:1) mixture. The prepared emulsion was incubated during 2 hours at t=65° C., then phenol-chloroform mixture was separated by centrifuging (500 g during 20 minutes, room temperature).

The procedure of deproteinisation with phenol—chlorophorm mixture was repeated 3 times, and then the water phase was processed with chloroform and diethyl ether. Separation from organic solvents was made by centrifugation at 5000 g during 15 minutes). Then equal volume of izopropanol was added to resulting aqueous phase and the mixture was incubated overnight at 0° C. After sedimentation the nucleic acids were separated by centrifugation at 10000 g during 30 minutes. The sediment of nucleic acids was dissolved in of 10 mM tris-HCl buffer, pH 7, 6 with 5 mM EDTA, and inflicted to the CsCl gradient (1M, 2.5M, 5.7M) in test-tube for rotor SW60Ti. The volume of DNA solution was 2 ml, volume of each step of CsCl was 1 ml. Ultracentrifugation was conducted in L80-80 (Beckman) centrifuge during 3 hours at 250000 g. DNA was collected from the surface of each gradient step into fractions. These fractions were dialyzed during 12 hours (t=4° C.). Presence of DNA in fractions was determined by agar electrophoresis and DNA was visualized by ethidium bromide staining. The amount of DNA was determined with specrophotometer (Beckman DU70) in cuvet (100 mcl) at wavelength of 220-230 nm.

Mice Lewis lung carcinoma and Erlich carcinoma were used in experiments. Cells were cultivated in RPMI-1640 medium with 10% calf serum and 1% penicillin-streptomycin in atmosphere of 5% $CO_2$.

For tumors inoculation in mice the cells were cultivated till monolayer is formed, then detached with tripsin-EDTA buffer. The cells were washed 3 times by centrifuging in phosphate buffer and then resuspended up to 0, $5*10^7$/ml concentration in the same buffer. The cell viability was determined with metylene blue staining in haemocitometer. Cells suspensions with no less than 95% of living cell were used for transplantation.

C57B1 mice and white randomly breeded mice from "Rappolovo" animal house were used. Weight of animals was 24-26 g. 6-7animals were kept in one cage on a standard diet without limitation of water. LLC cells in dose $5*10^5$ per mice in 0,1 ml of phosphate buffer were transplanted into thigh soft tissues. Erlich tumors were transplanted by administration of 0,2 ml of 10% cell suspension in physiological solution.

In some experiments level of extracellular DNA in blood plasma was quantified. DNA was isolated according to aforesaid protocol. The DNA level was measured with PicoGreen kit. Electrophoresis of extracellular blood DNA was performed with 1% agar gel. DNA was visualized with etidium-bromide solution. The levels of high molecular DNA fraction (more than 300 base pairs) were determined by densitometry. Lambda phage DNA, digested with EcoRI and HindIII was used as electrophoresis marker.

EXAMPLE 1

Iinhibition of Erlich Carcinoma Growth

Recombinant human DNAase 1 (Genentech) was used.

1 group: 10 mice bearing Erlich carcinoma was used as control. The mice were injected with 0,2 ml of phosphate buffer intraperitoneally twice a day every day from day 3 to day 7 after the tumor cell transplantation.

2 group: 10 mice bearing Erlich carcinoma were introduced with intraperitoneal injections of DNAase in dose of 1 mg/kg of body weight in 0,2 ml of phosphate buffer four times daily every day from day 3 to day 7 after the tumor cell transplantation.

3 group: 10 mice bearing Erlich carcinoma were administered with intraperitoneal injections of DNAase in dose of 0,5 mg/kg of body weight in 0,2 ml of phosphate buffer four times daily every day from day 3 to day 7 after the tumor cell transplantation.

4 group: 10 mice bearing Erlich carcinoma were administered with intraperitoneal injections of DNAase in dose of 0,1 mg/kg of body weight in 0,2 ml of phosphate buffer four times daily every day from day 3 to day 7 after the tumor cell transplantation.

5 group: 10 mice bearing Erlich carcinoma were administered with intraperitoneal injections of DNAase in dose of 0,05 mg/kg of body weight in 0,2 ml of phosphate buffer four times daily every day from day 3 to day 7 after the tumor cell transplantation. The results were evaluated as tumor Growth Inhibitory Index(GII) (%) at the last day of DNAase injections. The quantification of blood plasma extracellular DNA and it's electrophoretic qualification were also performed.

The results are presented in the table 1.

Tumor size, extracellular DNA level and extracellular DNA electrophoresis profile on day 7 after tumor transplantation.

TABLE 1

| Group | Tumor volume | Inhibition (%) | Extracellular DNA level, (ng/ml) | Presence of high molecular fractions of extracellular DNA |
|---|---|---|---|---|
| Control | 98 +/− 14 | — | 104.8 | 100%* |
| 1 mg/kg\ | 23 +/− 6 | 76% | 38.3 | 0 |
| 0.5 mg/kg | 32 +/− 6 | 67% | 55.1 | 25% |
| 0.1 mg/kg | 58 +/− 12 | 37% | 78.0 | 70% |
| 0.05 mg/kg | 87 +/− 11 | 10% | 98.7 | 100% |

*The control group electrophoretic density were considered as 100%.

The presented data demonstrated that sufficiently high doses of DNAase 1 are needed to achieve the better therapeutic effect.

EXAMPLE 2

Iinhibition of Erlich Carcinoma Growth

Recombinant human DNAase I (Genentech) was used.
5 groups of mice bearing LLC were used.
1 group-7 mice-the control.

2 group-6 mice were administered with intraperitoneal injections of DNAase in dose of 1 mg/kg of body weight twice a day every day from day 3 to day 5 after the tumor cell transplantation.

3 group-6 mice were administered with intraperitoneal injections of DNAase in dose of 1 mg/kg of body weight twice a day every day from day 3 to day 10 after the tumor cell transplantation.

4 group-6 mice were administered with intraperitoneal injections of DNAase in dose of 1 mg/kg of body weight twice a day every day from day 3 to day 15 after the tumor cell transplantation.

5 group-6 mice were administered with intraperitoneal injections of DNAase in dose of 1 mg/kg of body weight twice a day every day from day 3 to day 18 after the tumor cell transplantation.

6 group-6 mice were administered with intraperitoneal injections of DNAase in dose of 1 mg/kg of body weight twice a day every day on 3,5,7,9,11,13,15 and 17 day after the tumor cell transplantation.

7 group-6 mice were administered with intraperitoneal injections of DNAase in dose of 0,5 mg/kg of body weight four times daily every day from day 3 to day 10 after the tumor cell transplantation. The results was evaluated as animal survival on day 30 and day 50 after the tumor cell transplantation. The results are presented in the table 2.

Animal survival on day 30 and day 50 after the tumor cell transplantation.

TABLE 2

| Group | day 30 (amount of alive/dead animals in group) | day 50 (amount of alive/dead animals in group) |
|---|---|---|
| 1 | 0-7 | 0-7 |
| 2 | 0-6 | 0-6 |
| 3 | 3-3 | 0-6 |
| 4 | 5-1 | 3-3 |
| 5 | 6-0 | 6-0 |
| 6 | 0-6 | 0-6 |
| 7 | 4-2 | 1-5 |

The presented data demonstrated that the therapy efficacy increases as the treatment time extends. The therapy efficacy is decrease if it is not uninterrupted. Multiple-dose administration is preferred.

EXAMPLE 3

Lung Carcinoma Treatment 54-years-old man has been admitted to the hospital with diagnosis of lung carcinoma.

By patient's agreement, due to lack of any available treatment modality, subcutaneous injections of dornaze—alpha were prescribed. The treatment began with administration of daily dose of 50 mkg/kg. Every consecutive day blood extracellular DNA level was measured and blood extracellular DNA was fractioned by electrophoresis. Once a week the primary tumor site and metastases were checked with X-rays and NMR-tomography. After initial 7 day period the dornaze-alpha daily dose has been increased up to 100 mkg/kg because of no changes in level and electrophoresis pattern of blood extracellular DNA and no reactions from primary site of the tumor and the metastases. Because of no changes after another 7 days the dosing has been increased up to 150 mkg/kg. Two days after the first injection of the preparation in dose 150 mkg/kg the material recession (more than 50%) of the blood extracellular DNA fraction with the size more than 300 base pairs has been observed although total amount of extracellular DNA has not been greatly decreased (less than 20%). During the next 4 days the patient's general condition has noticeably improved and on day 7 of this cycle of therapy 25%-decreasing of primary tumor lesion size and signs of regression of two bone metastases have been shown by NMR-scanning and X-ray examination. The probes of patient's extracellular DNA taken before the treatment started and 21 days after the beginning the therapy were cloned by means a method which allowed to construct non amplificated plasmid libraries of blood extracellular DNA with representativeness up to one million of clones with the average size of 300-500 base pairs. The DNA which have been isolated with aforesaid protocol was additionally deproteinizated with proteinase K (Sigma) at t=65 C for the removing of firm-binded proteins. After the deproteinization and single-stage treatment of phenol-chloroform mixture (t=65° C.) DNA was precipitated overnight with 2,5 volumes of ethanol. Then DNA was treated by Eco RI restrictase during 3 hours or by Pfu polymerase (Stratagene) in presence of 300 mkM of all desoxy-nucleotidtriphosphates for sticky-ends elimination. The completed DNA was phosphorylated by polynucleotidkinase T4 (30U, 2 h.). The preparations were ligated to pBluescript plasmide (Stratagene), which had been digested with EcoRI or PvuII and dephosphorylated by phosphatase CIP (Fermentas) during 1 hour. 1 mkg of vector and 0,1-0,5 mkg of serum DNA were used. The process of ligation was conducted with Rapid Legation Kit (Roche) during 10 hours at T=16° C. The volume of this mixture was 50 mkl. The ligated library was transformed into DH12S cells (Life Technologies) by meant of electroporator E. Coli porator (BioRad). 12-20 electroporation covets were used for the transformation of one library. The library serial dilutions of $10^{-4}$, $10^{-5}$ and $10^{-6}$ were cloned on 1,5% agar and LB media supplemented with 100 mkg/ml of ampicilline. In both cases the libraries represented $2-3*10^6$ clones.

Analysis of 96 randomly selected clones with the size 300-1000 base pairs from the "before treatment" library showed that 55 from 96 clones were the unique sequences of human DNA. For the 15 sequences from 55 the gene function or corresponding gene product were identified with Human-GeneBank.

| Gene or corresponding protein product | Reported role in cancerogenesis and cancer progression |
|---|---|
| G-protein coupled receptor protein | Key role in neoplastic transformation, apoptosis inhibition, hormone independence and metastasis |
| Snf2 coupled CBP activator (SCARP) | Transcription activator, reported in synovial sarcoma and leukemia. |
| SRY-box containing gene | Transcription modulator expressed in embryogenesis. Reported in medulloblastoma, gonadal tumors, highly metastatic melanoma. |
| Tyrosine kinase | Key role in cancer cell regulation network. Some class homologues are the products of cellular oncogenes. |
| Fibroblast activation protein, cell surface protease | Involved into cancer invasion and metastasis. |
| Brain testican | Reported in embryonic rhabdomyosarcoma. |
| KRAB domain, Zn-finger protein. | Reported in early embryogenesis, neuroblastoma, Ewing sarcoma, T-cell lymphoma, linked with acquisition of drug resistance in lung cancer. |
| Melanoma associated antigen | Antigen expressed in melanoma cells. |
| N-cadherin | Involved into cancer invasion and metastasis. |
| Interleukin 7 | Proposed essential autocrine - paracrine growth factor for many cancers |
| DEAD Box RNA helicase-like protein | Expressed in highly proliferating and cancer cells. |
| Lipin-1 | Involved into cancer cell response to cytotoxic drugs. |
| Dynein | Participate in p53 intracellular traffic, reported in prostate cancer and hepatocellular carcinoma. |
| Ramp protein | Reported in human embryonic carcinoma |

Analysis of 100 clones selected randomly from the "21 day after treatment" library showed that more than 90% sequences of clones represented short fragments of repetitive DNA of human genome with dominance of alpha-satellite DNA.

Hence the use of DNAase in doses which are sufficient for destroying extracellular blood DNA with size higher than 300 base pairs leads to disappearing of unique fragments of human genome from extracellular blood DNA, including those involved into development and maintenance of cancer cells malignant behavior. At the same time the tumor respond to applied therapy.

EXAMPLE 4

The treatment of malignant low differentiated lymphoma invading the spleen and portal vien and metastases in the liver.

49-years-old woman has been admitted to the hospital with the fever (39 C), progressive jaundice, liver failure and being under suspicion of acute hepatitis suffering. During the inspection malignant lymphoma with the difflusely defeats of spleen and gates of liver and multiply metastases in liver were revealed. By patient's agreement, due to the lack of any specific treatment and because of progressing of the disease, intravenous injections of bovine pancreatic DNAase were prescribed. Twice a day measuring of level of blood extracellular DNA and it's electrophoretic fractioning were conducted. During the first day 500000 units of enzyme were administered as 26-hour infusions. Later this dose was increased by 1 000 000 units per day. When the dose was 5500000 units daily the 50% decrease of blood extracellular DNA and disappearance of fraction of DNA with size more than 300 base pairs were noted. As the continued DNA infusions at 5500000 units per day were being performed the patient's general condition was being improved, fever and jaundice disappeared, biochemical indexes of blood taken a turn to the better. Control Doppler examination which has been made at day 20 after the beginning of the treatment showed significant reduction (more than 40%) of lesion in the spleen and disappearance of more than half of all metastatic sites in the liver. The woman was moved to another hospital for conducting chemotherapy.

Hence the use of DNAase in doses which are sufficient for destroying extracellular DNA of blood with size higher than 300 base pairs leads to tumor regression according to the inventive method.

EXAMPLE 5

The study of influence of polyclonal serum containing the antibodies against DNA on the growth of Erlich carcinoma of in mice treating with DNAase.

Antibodies against DNA were isolated from the blood of patients with systemic lupus erythematosus according to method of Shuster. A. M. (Shuster A. M. et. al., Science, v. 256, 1992, pp. 665-667). Such anti-DNA antibodies could not only bind DNA but also hydrolyze it. Human recombinant DNAase I(Genetech) was used.

1 group-7 mice bearing Erlich carcinoma—control 2 group-6 mice bearing Erlich carcinoma and being have got intravenous injection of human anti-DNA antibodies (Ig G) in dose of 200 mkg per animal on day 3 after the carcinoma transpalantation Mice also have been administered with DNAase in dose 0, 5 mg/kg 4 times intraperitonealy a day from day 3 to day 7 after the tumor transplantation.

3 group-6 mice bearing Erlich carcinoma and being have got intravenous injection of human non-specific immunoglobulin (Ig G) in dose of 200 mkg per animal on day 3 after the carcinoma transpalantation. Mice also have been administered with DNAase in dose 0, 5 mg/kg 4 times intraperitonealy a day from day 3 to day 7 after the tumor transplantation.

4 group-6 mice bearing Erlich carcinoma and being have got intraperitoneal treatment of human DNAase in dose of 0,5 mg/kg 4 times intraperitonealy a day from day 3 to day 7 after the tumor transplantation.

The effect was evaluated as the tumor growth inhibition on day 7 after the tumor cell transplantation (TGI, evaluated in percents). The results are presented in the table 3.

The tumor volume on day 7 after tumor transplantation

TABLE 3

| Group | Tumor volume | T % |
|---|---|---|
| 1 | 105 +/− 12 | — |
| 2 | 25 +/− 5 | ~75% |
| 3 | 37 +/− 6 | ~66% |
| 4 | 35 +/− 7 | ~67% |

The presented data demonstrated that the combined therapy with DNAase and the agent binding blood exracellular DNA has more noticeable antitumor effect.

EXAMPLE 6

The study of degradation kinetics of high molecular weight fraction (size more than 300 pairs of bases) of blood extracellular DNA of breast cancer patient in presence of: bovine pancreatic DNAase, Proteinase K and bovine pancreatic DNAase, Lipase and bovine pancreatic DNAase and extracellular desoxyrybonuclease Serratia Mercenses, which has ribonuclease activity and is as destroyed and modificating agent at the same time.

The respective enzyme was added to a sample of patient's plasma and incubated for 45 minutes at 37° C. 45 minutes later the reaction has being stopped and isolation and electrophoretic fractioning with densitometry of blood extracellular DNA have being performed.

The results are presented in the table 4.

Degradation kinetics of high molecular fraction

TABLE 4

| The way of working | Degradation of high molecular fraction, % |
|---|---|
| Intact control | 0 |
| Proteinase K (0.1 mkg/ml) | 0 |
| Pancreatic lipase (0.1 mkg/ml) | 0 |
| Bovine pancreatic DNAase (1 Kuntz Units/ml) | 25 |
| Bovine pancreatic DNAase (1 Kuntz Units\ml) + proteinase K (0.1 mkg\ml) | 35 |
| Bovine pancreatic DNAase (1 Kuntz Units/ml) + pancreatic lipase (0.1 mkg/ml) | 40 |
| Extracellular desoxyribonuclease of Serratia Mercenses (1 Kuntz Units/ml) | 45 |

The presented data demonstrated that the combined therapy with DNAase and the agent modificating blood exracellular DNA binding with proteins, lipids and ribonucleic acids leads to more effective degradation of high molecular fraction (size more than 300 pairs of bases) of blood extracellular DNA

EXAMPLE 7

The study of the influence of different methods of destroying extracellular DNA on it's pathogenic properties.

C57B1 mice have been inoculated with high metastatic or low metastatic strain of LLC tumor. On the 9 th day after the inoculation animals were euthanized and pool of their blood plasma was collected. The summary fraction of extracellular blood plasma DNA was kept in phosphate buffer at t=−20° C.).

7 groups of mice inoculated with low metastatic strain of LLC were included in the experiment.

1 group-6 mice grafted by low metastatic LLC strain.

2 group-6 mice grafted by low metastatic LLC strain and were subjected to twice repeated intravenous administration (on 7 and 8 day after inoculation) of summary fraction of extracellular DNA from mice grafted by high metastatic strain (before the administration 0,05 mkg of DNA have been dissolved in 500 mkl of fresh heparinized blood)

3 group-6 mice grafted by low metastatic LLC strain and were subjected to twice repeated intravenous administration (on 7 and 8 day after inoculation) of summary fraction of extracellular DNA from mice grafted by high metastatic strain (before the administration 0,05 mkg of DNA have been dissolved in 500 mkl of fresh heparinized blood). Before the administration the sample with DNA has been disinfected photochemically (by adding 1 mkM of methylen blue stain and exposure of red light during 10 min (~60 000 lux).

4 group-6 mice grafted by low metastatic LLC strain and were subjected to twice repeated intravenous administration (on 7 and 8 day after inoculation) of summary fraction of extracellular DNA from mice grafted by high metastatic strain (before the administration 0,05 mkg of DNA have been dissolved in 500 mkl of fresh heparinized blood). Before the administration the sample with DNA has been mixed with 10 mkg of hydrolytic anti-DNA antibodies.

5 group-6 mice grafted by low metastatic LLC strain and were subjected to twice repeated intravenous administration (on 7 and 8 day after inoculation) of summary fraction of extracellular DNA of mice graft by high metastatic strain (before the administration 0,05 mkg of DNA have been dissolved in 500 mkl of fresh heparinized blood). Before the administration 1 mkg of the fragment A of the plant toxin Ricin was added to the sample and the mixture was incubated during 1 hour at =37° C. Ricin is the representative of RIP-toxins family (proteins inactivating ribosomes) which widely used for immunotoxins' development. In addition to its capability to inactivate ribosomes these proteins also can deadenilate and hydrolyze DNA. To realize of the toxic effect the unit A of the type II RIP toxin should be delivered into cell by unit B. In absence of subunit B chain A is not toxic, however polyadeninglicosidase activity of chain A can be used for destruction of DNA circulating in blood.

6 group-6 mice grafted by low metastatic LLC strain were subjected to twice repeated intravenous administration (on 7 and 8 day after inoculation) of summary fraction of extracellular DNA from mice grafted by high metastatic strain (before the administration 0,05 mkg of DNA have been dissolved in 500 mkl of fresh heparinized blood). The DNA sample was enzymatically methylated before the administration. (I. Muiznieks et. al., FEBS Letters, 1994, v. 344, pp. 251-254).

7 group-6 mice grafted by low metastatic LLC strain were subjected to twice repeated intravenous administration (on 7 and 8 day after inoculation) of summary fraction of extracellular DNA of mice graft by low metastatic strain 8 group-6 mice grafted by low metastatic LLC strain were subjected to twice repeated intravenous administration (on 7 and 8 day after inoculation) of summary fraction of extracellular DNA of mice grafted by high metastatic strain (before the administration 0,05 mkg of DNA have been dissolved in 500 mkl of fresh heparinized blood). The sample with DNA was incubated with 200 ng/ml of dornase alpha during 30 minutes at T=37° C. before the administration.

The number of lung metastases (N cp) was evaluated on day 15 after the inoculation.

The results are presented in the table 5.

The number of lung metastases on day 15 after the tumor inoculation subjectto the extracellular DNA destruction method.

TABLE 5

| Group | N cp |
|-------|------|
| 1 | 12.0 |
| 2 | 22.5 |
| 3 | 14.1 |
| 4 | 15.5 |
| 5 | 15.1 |
| 6 | 12.3 |
| 7 | 13.3 |
| 8 | 13.5 |

Hence blood extracellular DNA of mice bearing highly malignant tumor strain increases metastasis of less malignant tumor. Destruction, binding and modification of blood extracellular DNA suppress that process according to the inventive method.

INDUSTRIAL APPLICABILITY

For the realization the methods there were used well-known materials and equipment manufactured in plant conditions and according to aforesaid the invention conformances to requirements of "industrial applicability" criteria (IA).

The invention claimed is:

1. A method of treatment for lung carcinoma, and malignant and low differentiated lymphomia, said method comprises a step of introducing a treatment agent into a circulating blood system of a cancer patient diagnosed with at least one of the said cancers and diseases, said treatment agent destroys extracellular DNA in said blood of said cancer patient, wherein said treatment agent used to destroy said extracellutar DNA is a DNAse enzyme; and wherein said treatment agent is administered in doses and regiments which provide blood plasma DNA-hydrolytic activity,—measured in blood plasma, to exceed 150 Kunitz units per liter of plasma during more than 12 hours in total within 24 hours.

2. The method according to claim 1, wherein doses of said treatment are introduced to the patient according to a regime schedule which is carried out continuously for no less than 48 hours.

3. The method according to claim 1, wherein bovine pancratic DNase is said agent used to destroy said extracellular DNA, said bovine pancreatic DNAsc is parenterally introduced in doses ranging from 50,000 Kunitz units to 250,000,000 Kunitz units a day for 5-360 days.

4. The method according to claim 1, wherein human recombinant DNAse is used.

5. The method according to claim 4, wherein human recombinant DNAse 1 (Domase alpha) is parenterally introduced in doses 1,15 mg/kg-500 mg/kg of body weight daily during 5-360 days.

6. The method according to claim 1, wherein the treatment is carried out from a diagnosis of the cancer and to a remaining term of the patient's life.

7. The method according to claim 1, further including a step of introducing a binding agent into said blood system, said binding agent binds said extracellular DNA, wherein said binding agent is anti-DNA antibodies.

* * * * *

UNITED STATES PATENT AND TRADEMARK OFFICE
CERTIFICATE OF CORRECTION

| | | |
|---|---|---|
| PATENT NO. | : 7,612,032 B2 | Page 1 of 2 |
| APPLICATION NO. | : 10/564861 | |
| DATED | : November 3, 2009 | |
| INVENTOR(S) | : Dmitry Dmitrievich Genkin et al. | |

It is certified that error appears in the above-identified patent and that said Letters Patent is hereby corrected as shown below:

Page 7, (column 11, line 31) - delete "1. A method of treatment for lung carcinoma, and malignant and low differentiated lymphomia, said method comprises a step of introducing a treatment agent into a circulating blood system of a cancer patient diagnosed with at least one of the said cancers and diseases, said treatment agent destroys extracellular DNA in said blood of said cancer patient, wherein said treatment agent used to destroy said extracellular DNA is a DNAse enzyme; and wherein said treatement agent is administered in doses and regiments which provide blood plasma DNA-hydrolytic activity, - measured in blood plasma, to exceed 150 Kunitz units per liter of plasma during more than 12 hours in total within 24 hours." and insert -- 1. A method of treating lung carcinoma or malignant and low differentiated lymphoma comprising parenterally administering to a patient in need thereof DNAse in doses and regimens which provide blood plasma DNA-hydrolytic activity, measured in blood plasma, to exceed 150 Kunitz units per liter of plasma during more than 12 hours in total within 24 hours. --

Page 7, (column 12, line 10) - delete "2. The method according to claim 1, wherein doses of said treatment are introduced to the patient according to a regime schedule which is carried out continuously for no less than 48 hours." and insert -- 2. The method according to claim 1, wherein said doses of DNAse are administered to the patient according to a regime schedule which is carried out continuously for no less than 48 hours. --

Page 7, (column 12, line 14) - delete "3. The method according to claim 1, wherein bovine pancratic DNase is said agent used to destroy said extracellular DNA, said bovine pancreatic DNAsc is parenterally introduced in doses ranging from 50,000 Kunitz units to 250,000,000 Kunits units a day for 5-360 days." and insert -- 3. The method according to claim 1, wherein the DNAse is bovine pancreatic DNAse, and the dose is from 50,000 Kunitz units to 250,000,000 Kunitz units a day for 5-360 days. --

Page 7, (column 12, line 19) - delete "4. A method according to claim 1, wherein human recombinant DNAse is used." and insert -- 4. The method according to claim 1, wherein the DNAse is human recombinant DNAse I. --

Signed and Sealed this
Thirtieth Day of August, 2011

David J. Kappos
*Director of the United States Patent and Trademark Office*

CERTIFICATE OF CORRECTION (continued)
U.S. Pat. No. 7,612,032 B2

Page 7, (column 12, line 21) - delete "5. The method according to claim 4, wherein human recombinant DNAse 1 (Domase alpha) is parenterally introduced in doses 1,15 mg/kg-500 mg/kg of body weight daily during 5-360 days." and insert -- 5. The method according to claim 4, wherein the human recombinant DNAse I is administered at a dose of 0.15 mg/kg - 500 mg/kg of body weight daily for 5-360 days. --

Page 7, (column 12, line 25) - delete "6. The method according to claim 1, wherein the treatment is carried out from a diagnosis of the cancer and to a remaining term of the patient's life." and insert -- 6. The method according to claim 1, wherein the administering is carried out for the remaining term of the patient's life. --

Page 7, (column 12, line 28) - delete "7. The method according to claim 1, further including a step of introducing a binding agent into said blood system, said binding agent binds said extracellular DNA, wherein said binding agent is anti-DNA antibodies." and insert -- 7. The method according to claim 1, further comprising parenterally administering to said patient anti-DNA antibodies. --